United States Patent
Foley et al.

(10) Patent No.: US 10,011,582 B2
(45) Date of Patent: Jul. 3, 2018

(54) SUBSTITUTED DELTA-LACTONES AND METHODS OF PREPARING SAME

(71) Applicant: P2 Science, Inc., Woodbridge, CT (US)

(72) Inventors: Patrick Foley, New Haven, CT (US); Yonghua Yang, New Haven, CT (US)

(73) Assignee: P2 SCIENCE, INC., Woodbridge, CT (US)

( * ) Notice: Subject to any disclaimer, the term of this patent is extended or adjusted under 35 U.S.C. 154(b) by 0 days.

(21) Appl. No.: 15/119,539

(22) PCT Filed: Feb. 18, 2015

(86) PCT No.: PCT/US2015/016371
§ 371 (c)(1),
(2) Date: Aug. 17, 2016

(87) PCT Pub. No.: WO2015/126936
PCT Pub. Date: Aug. 27, 2015

(65) Prior Publication Data
US 2017/0057940 A1  Mar. 2, 2017

Related U.S. Application Data

(60) Provisional application No. 61/941,912, filed on Feb. 19, 2014.

(51) Int. Cl.
C07D 309/30 (2006.01)
C07D 309/32 (2006.01)

(52) U.S. Cl.
CPC ......... *C07D 309/32* (2013.01); *C07D 309/30* (2013.01)

(58) Field of Classification Search
CPC .......................... C07D 309/30; C07D 309/32
See application file for complete search history.

(56) References Cited

U.S. PATENT DOCUMENTS

2013/0078685 A1   3/2013   Ullrich et al.

FOREIGN PATENT DOCUMENTS

| CN | 102653531 A | 9/2012 |
|---|---|---|
| WO | WO 2007/068498 A1 | 6/2007 |
| WO | WO 2015/126936 A1 | 8/2015 |

OTHER PUBLICATIONS

Abe et al., 75 Nippon Kagaka Kaishi, Pure Chem. (1921-47) 953-5 (1954) (CAS Abstract).*
Cahn, R. S. et al. "Specification of Molecular Chirality" *Angew. Chem. Inter. Edit.* 1966, vol. 5, No. 4, p. 385-415.
Cahn, R. S. and Ingold, C. K. "Specification of Configuration About Quadricovalent Asymmetric Atoms" *J. Chem. Soc.* 1951 (London), p. 612-622.
Cahn, R. S. et al. "The Specification of Asymmetric Configuration in Organic Chemistry" *Experientia* 1956, vol. 12, p. 81-94.
Cahn, R. S. "An Introduction to the Sequence Rule. A System for the Specification of Absolute Configuration" *Journal of Chemical Education* 1964 (London), vol. 41, No. 3, p. 116-125.
Cermak, S. C. and Isbell, T. A. "Synthesis of δ-Stearolactone from Oleic Acid" *JAOCS*, vol. 77, No. 3, (2000), p. 243-248.
Cook, C. et al. "Study of the Total Synthesis of (−)-Exiguolide" *J. Org. Chem.* 2012, 77, p. 6728-6742.
Dupe, A. et al. "Methyl Ricinoleate as Platform Chemical for Simultaneous Production of Fine Chemicals and Polymer Precursors" *ChemSusChem.* 2012, vol. 5, p. 2249-2254.
Förtsch, W. et al. "Synthesis, Crystal Structure, and Reactions of Novel Metallacyclic Dioxo- and Aminooxocarbene Complexes of Iron" *Chem. Ber.* 1994, vol. 127, p. 711-715.
Gerth, D. B. and Giese, B. "Synthesis of δ-Lactones via Radical C-C Bond Formation Using Chiral Radical Precursors" *J. Org. Chem.* 51 (1986), p. 3726-3729.
Kadesch, R. G. "Ozonolysis of Fatty Acids and Their Derivatives" *Progress in the Chemistry of Fats and Other Lipids* 1963, vol. 6, p. 291-312.
Kula, J. et al. "Synthesis of Enantiomerically Pure Volatile Compounds Derived From (R)3-Hydroxynonanal" *Tetrahedron: Asymmetry* 11 (2000), p. 943-950.
Surburg, H. and Panten, J. *Common Fragrance and Flavor Materials*, 5th. Ed. Wiley-VCH, 2006, p. 149-172.
Rosenberger, M. et al. "28. Synthesis of δ-Lactones From Glutaraldehyde" *Helvetica Chimica Acta* 1972, vol. 55, p. 249-255.
Sabitha, G. et al. "The First Asymmetric Total Synthesis of (R)-Tuberolactone, (S)-Jasmine Lactone and (R)-δ-Decalactone" *Tetrahedron Letters* 47 (2006), p. 8179-8181.
Schiaffo, C. E. "I. An Improved Procedure for Alkene Ozonolysis. II. Exploring a New Structural Paradigm for Peroxide Antimalarials", *Student Research Projects, Dissertations, and Theses—Chemistry, Department. University of Nebraska-Lincoln*, Jun. 2011, Paper 23.
Tanaka, T. et al. "Syntheses of (5E)-PGE$_2$ and New 6-Functionalized Derivatives by the Use of Palladium-Catalyzed Decarboxylative Allylic Alkylation" *Tetrahedron* vol. 42, No. 24, (1986), p. 6747-6758.
Shao, L. et al. "Asymmetric Hydrogenation of 3,5-Dioxoesters Catalyzed by Ru-binap Complex: A Short Step Asymmetric Synthesis of 6-Substituted 5,6-dihydro-2-pyrones" *Tetrahedron* vol. 49, No. 10, (1993), p. 1997-2010.
Utaka, M. et al., "New Synthesis of Jasmine Lactone and Related δ-Lactones from 1,2 Cyclohexanedione. Preparation and Dye-Sensitized Photooxygenation of 3-(2-Alkenyl)- and 3-(2-Alkynyl)-1,2-cyclohexanediones" *J. Org. Chem.* 1986, vol. 51, No. 6, p. 935-938.
Chmielewski, et al., "Organic Syntheses Under High Pressure. 3. General Approach to the Synthesis of Naturally Occuring .delta.-lactones," *The Journal of Organic Chemistry*, vol. 46, No. 11 (1981) pp. 2230-2233.

(Continued)

*Primary Examiner* — Timothy R Rozof
(74) *Attorney, Agent, or Firm* — Hoxie & Associates LLC

(57) ABSTRACT

The invention relates to substituted delta-lactones as well as to processes for synthesizing them, e.g., using fatty acids as starting material.

22 Claims, No Drawings

(56) References Cited

OTHER PUBLICATIONS

Otsubo, et al., "A Direct Synthesis of [gamma]-, [delta], and [epsilon]-Lactones Utilizing SmI2-induced Barbier-type Reaction in the Presence of Hexamethylphosphoric Triamide (HMPA)," *Chemistry Letters*, (1987) p. 1487-1490 http://www.journal.csj.jp/doi/pdf/10.1246/cl.1987.1487 [retrieved on May 29, 2017].

\* cited by examiner

SUBSTITUTED DELTA-LACTONES AND METHODS OF PREPARING SAME

RELATED APPLICATIONS

This application is a U.S. National Phase application, filed under 35 U.S.C. § 371(c), of International Application No. PCT/US2015/016371, filed Feb. 18, 2015, which claims the benefit of and priority to U.S. Provisional Application No. 61/941,912, filed on Feb. 19, 2014, the entireties of each of which are hereby incorporated by reference for all purposes.

BACKGROUND OF THE INVENTION

Delta-lactones, such as 5-substituted delta-lactones, are important flavor and aroma constituents and are found in many natural products. These compounds can be used either directly or as intermediates in the flavor, fragrance, pharmaceutical, and cosmetic industries. For example, delta-decalactone and delta-dodecalactone are used in coconut and butter flavorings, respectively; jasmine lactone (5-hydroxy-7-decenoic acid delta-lactone) and jasmolactone (tetrahydro-6-(3-pentenyl)-2H-pyran-2-one) are key jasmine fragrance ingredients; and massoia lactone ((R)-5,6-dihydro-6-pentyl-2H-pyran-2-one), a naturally-occurring, unsaturated decalactone is extracted from the bark of the Massoia tree at great expense for its desirable flavor profile.

Previous preparations of 5-substituted delta-lactones often require labor intensive multistep syntheses and/or use of petrochemicals as starting materials.

This invention relates to cost-effective methods of producing 5-substituted delta-lactones using easily accessible renewable, biologically-derived feedstock and application thereof in the industry of, e.g., flavors, fragrances, pharmaceuticals and/or cosmetics.

SUMMARY OF THE INVENTION

In one aspect, the invention relates to a method of producing a delta-lactone compound of formula A:

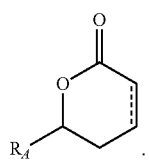

(A)

In this formula, the ===== is a single bond or a double bond and $R_4$ is unsubstituted or substituted $C_1$-$C_{10}$ alkyl, unsubstituted or substituted $C_3$-$C_{20}$ cycloalkyl, unsubstituted or substituted $C_2$-$C_{10}$ alkenyl, or unsubstituted or substituted aryl.

When the ===== is a double bond, the compound is of formula I:

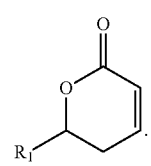

(I)

In formula I, $R_1$ is unsubstituted or substituted $C_1$-$C_{10}$ alkyl, unsubstituted or substituted $C_3$-$C_{20}$ cycloalkyl, unsubstituted or substituted $C_2$-$C_{10}$ alkenyl, or unsubstituted or substituted aryl, and the method includes:

reacting a compound of formula II:

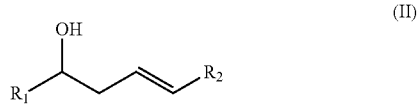

(II)

with ozone to obtain a compound of formula III;

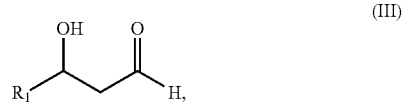

(III)

wherein $R_1$ is unsubstituted or substituted $C_1$-$C_{10}$ alkyl, unsubstituted or substituted $C_3$-$C_{20}$ cycloalkyl, unsubstituted or substituted $C_2$-$C_{10}$ alkenyl, or unsubstituted or substituted aryl and $R_2$ is H, unsubstituted or substituted $C_1$-$C_{20}$ alkyl, or unsubstituted or substituted $C_2$-$C_{20}$ alkenyl;

reacting the compound of formula III with a compound of formula IV:

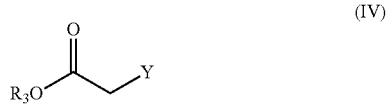

(IV)

in the presence of a metal to produce a reaction mixture, wherein Y is halo and $R_3$ is unsubstituted or substituted $C_1$-$C_{20}$ alkyl unsubstituted or substituted $C_2$-$C_{20}$ alkenyl, or unsubstituted or substituted aryl; and optionally treating the reaction mixture with an acid and/or heat to obtain the compound of formula I.

When the ===== is a single bond, the compound is of formula V:

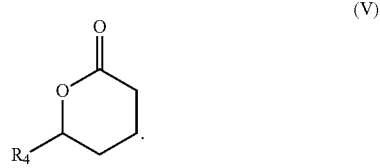

(V)

In formula V, $R_4$ is unsubstituted or substituted $C_1$-$C_{10}$ alkyl, unsubstituted or substituted $C_3$-$C_{20}$ cycloalkyl, unsubstituted or substituted $C_2$-$C_{10}$ alkenyl, or unsubstituted or substituted aryl, and the method includes:

reacting a compound of formula VI

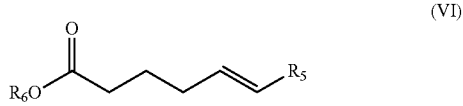

(VI)

with ozone to obtain a compound of formula VII;

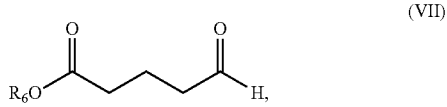
(VII)

wherein $R_5$ is unsubstituted or substituted $C_1$-$C_{20}$ alkyl or unsubstituted or substituted $C_2$-$C_{20}$ alkenyl and $R_6$ is unsubstituted or substituted $C_1$-$C_{10}$ alkyl;

reacting the compound of formula VII with a compound of formula VIII: $R^4$—X (VIII) in the presence of a metal to produce a reaction mixture, wherein X is halo and $R_4$ is unsubstituted or substituted $C_1$-$C_{10}$ alkyl, unsubstituted or substituted $C_3$-$C_{20}$ cycloalkyl, unsubstituted or substituted $C_2$-$C_{10}$ alkenyl, or unsubstituted or substituted aryl; and optionally treating the reaction mixture with an acid and/or heat to obtain the compound of formula V.

The invention also relates to a compound of formula I or a compound of formula V generated by the methods described herein.

The advantages of the methods of this invention include, but are not limited to, low costs, mild reaction conditions, improved yield of delta-lactones, and/or in certain cases, retention of stereochemistry.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. In addition, the materials, methods, and examples are illustrative only and are not intended to be limiting.

Other features and advantages of the invention will be apparent from the following detailed description and claims.

DETAILED DESCRIPTION OF THE INVENTION

5-Substituted delta-lactones are important flavor and aroma constituents and are found in many natural products. Previous preparations of 5-substituted delta-lactones often require labor intensive multistep syntheses, use of expensive catalysts, and/or use of petrochemicals as starting materials, see, e.g., Panten & Surburg, *Common Fragrance and Flavor Materials*, 2$^{nd}$. Ed. Wiley-VCH, p.165; Förtsch et al., *Chem. Ber.* 1994, 127, 711; Sabitha et al. *Tetrahedron Letters* 47(2006) 8179-8181; Saucy et al. *Helvetica Chimica Acta* 55 (1972) 249-255; Gerth & Giese, *J. Org. Chem.* 5/(1986) 3726-3729; Uchida et al. *Tetrahedron* 49 (1993) 1997-2010; Tanaka et al. *Tetrahedron* 42 (1986) 6747-6858; Bruneau et al. *ChemSusChem*, 5 (2012) 2249-2254; Kula et al. *Tetrahedron: Asymmetry* 11 (2000) 943-950; Cermak & Isbell *JAOCS*, 77 (2000) 243-248; and WO 2007/068498.

In one aspect, the invention relates to methods of producing 5-substituted delta-lactones using renewable, biologically-derived feedstock such as castor oil and oil of meadowfoam (*Limnathes alba*) seeds. In particular, the methods disclosed herein include ozonolysis of specific fatty acids and/or esters thereof to produce compound(s) having aldehyde functionalities, which can then readily form delta-lactones upon addition of an alkyl metal halide. For example, the fatty acids and/or esters thereof used for ozonolysis either possess a homoallylic alcohol, such as ricinoleic acid and esters thereof, or possess a degree of unsaturation at the 5-position, such as 5-eicosenoic acid, 5-docosenoic acid, and esters thereof. For example, the ozonolysis of the fatty acids and/or esters thereof is performed in an aqueous medium, and the resulting intermediates are then reduced in the presence of a reducing agent such as sodium bisulfite, or $H_2$ in the presence of a catalyst, such as Pd or Ni, thus generating the desired aldehydes. The aldehydes that result from the ozonolysis of ricinoleic acid and 5-unsaturated fatty acid or esters thereof are 3-(R)-hydroxynonanal (i.e., 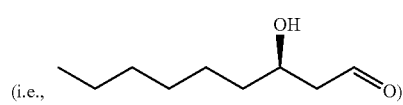)

and 5-oxopentanoic acid or esters thereof (i.e.,

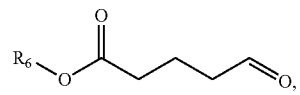), in which $R_6$ is as defined herein for formula VII), respectively. For example, the aldehydes are isolated either by distillation or extraction, and are then treated with, e.g., an alkylmetal halide, to form a C—C bond and a hydroxy/hydroxyl anion that can then undergo intramolecular cyclization with the corresponding ester or acid, either directly or after addition of heat and/or an acid. As an example, Scheme A below illustrates the transformation of fatty acids to the delta-lactones of interest.

Scheme A

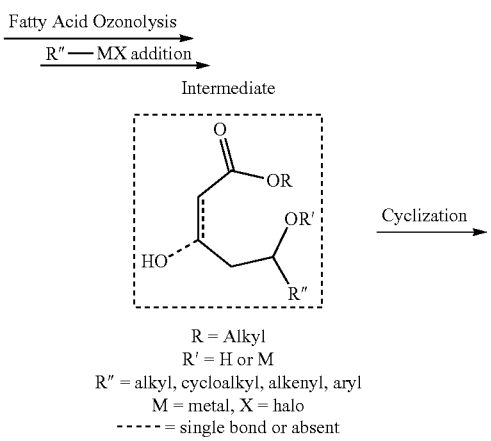

R = Alkyl
R' = H or M
R" = alkyl, cycloalkyl, alkenyl, aryl
M = metal, X = halo
- - - - - = single bond or absent Substituted Delta-Lactones

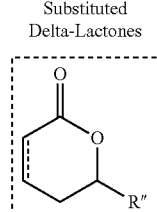

In one aspect, the invention features a method of synthesizing a compound of formula I:

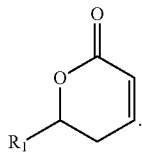
(I)

In formula I, $R_1$ is unsubstituted or substituted $C_1$-$C_{10}$ alkyl, unsubstituted or substituted $C_3$-$C_{20}$ cycloalkyl, unsubstituted or substituted $C_2$-$C_{10}$ alkenyl, or unsubstituted or substituted aryl, and the method includes:

reacting a compound of formula II:

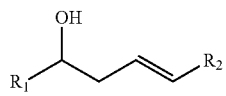
(II)

with ozone to obtain a compound of formula III;

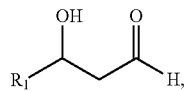
(III)

wherein $R_1$ is unsubstituted or substituted $C_1$-$C_{10}$ alkyl, unsubstituted or substituted $C_3$-$C_{20}$ cycloalkyl, unsubstituted or substituted $C_2$-$C_{10}$ alkenyl, or unsubstituted or substituted aryl and $R_2$ is H, unsubstituted or substituted $C_1$-$C_{20}$ alkyl, or unsubstituted or substituted $C_2$-$C_{20}$ alkenyl;

reacting the compound of formula III with a compound of formula IV:

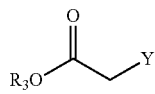
(IV)

in the presence of a metal to produce a reaction mixture, wherein Y is halo and $R_3$ is unsubstituted or substituted $C_1$-$C_{20}$ alkyl unsubstituted or substituted $C_2$-$C_{20}$ alkenyl, or unsubstituted or substituted aryl; and optionally treating the reaction mixture with an acid and/or heat to obtain the compound of formula I.

In one embodiment, $R_1$ is substituted or unsubstituted alkyl having 1, 2, 3, 4, 5, 6, 7, 8, 9, or 10 carbon atoms, or $R_1$ is substituted or unsubstituted alkenyl having 2, 3, 4, 5, 6, 7, 8, 9, or 10 carbon atoms and one, two, or three carbon-carbon double bonds. For example, $R_1$ is unsubstituted $C_1$-$C_{10}$ alkyl or unsubstituted $C_2$-$C_{10}$ alkenyl.

In one embodiment, $R_2$ is substituted or unsubstituted alkyl having 1, 2, 3, 4, 5, 6, 7, 8, 9, or 10 carbon atoms, or $R_2$ is substituted or unsubstituted alkenyl having 2, 3, 4, 5, 6, 7, 8, 9, or 10 carbon atoms and one, two, or three carbon-carbon double bonds. For example, $R_2$ is $C_1$-$C_{10}$ alkyl or $C_2$-$C_{10}$ alkenyl, each substituted with $COOR_a$, in which $R_a$ is H or unsubstituted or substituted alkyl having 1, 2, 3, 4, 5, 6, 7, 8, 9, or 10 carbon atoms.

In one embodiment, $R_3$ is substituted or unsubstituted alkyl having 1, 2, 3, 4, 5, or 6 carbon atoms. For example, $R_3$ is unsubstituted $C_1$-$C_6$ alkyl.

In one embodiment, Y is Cl or Br.

In one embodiment, the compound of formula II is ricinoleic acid or an ester thereof.

In one embodiment, the compound of formula III is 3-hydroxynonanal, e.g., 3-(R)-hydroxynonanal.

In one embodiment, the compound of formula I is 6-hexyl-5,6-dihydro-2H-pyran-2-one, e.g., (R)-6-hexyl-5,6-dihydro-2H-pyran-2-one.

In one embodiment, the compound of formula IV is ethyl bromoacetate or ethyl chloroacetate.

In one embodiment, the reaction of the compound of formula II with ozone is carried out in the presence of a solvent. For example, the solvent comprises water, an organic solvent or a mixture there of. For example, the organic solvent comprises an organic acid, e.g., an acid acetic acid, propionic acid, butyric acid, nonanoic acid, a fatty acid, or a mixture thereof.

In one embodiment, the reaction of the compound of the formula II with ozone is carried out in the absence of a solvent.

In one embodiment, the reaction of the compound of formula II with ozone is reductive ozonolysis, namely, the compound of formula II reacting with ozone and subsequently reacting with a reductant (i.e., a reducing agent). For example, the reductant used in the method is a reducing agent suitable for producing an aldehyde in a reductive ozonolysis process. For example, the reductant is $H_2$ in the presence or absence of a suitable catalyst, such as Pd, Ni, Rh, Pt, or Ru. For example, the reductant is sodium bisulfite ($NaHSO_3$). For example, the reductant is triphenylphosphine, thiourea, zinc dust, or dimethyl sulfide.

In one embodiment, the metal is zinc, lithium, magnesium, or copper.

In one embodiment, the reaction mixture from reacting the compound of formula III and the compound of formula IV is treated with an acid (e.g., hydrochloric acid), heat, or both, to obtain the compound of formula I.

In one embodiment, the reaction mixture from reacting the compound of formula III and the compound of formula IV is not treated with an acid or heat to obtain the compound of formula I.

In another aspect, the invention features a method of synthesizing compound of formula V:

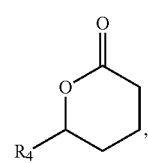
(V)

wherein $R_4$ is unsubstituted or substituted $C_1$-$C_{10}$ alkyl, unsubstituted or substituted $C_3$-$C_{20}$ cycloalkyl, unsubstituted or substituted $C_2$-$C_{10}$ alkenyl, or unsubstituted or substituted aryl, and the method includes:

reacting a compound of formula VI

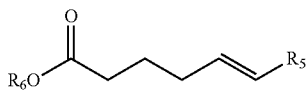

with ozone to obtain a compound of formula VII;

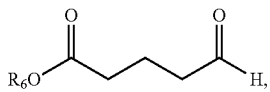

wherein $R_5$ is unsubstituted or substituted $C_1$-$C_{20}$ alkyl or unsubstituted or substituted $C_2$-$C_{20}$ alkenyl and $R_6$ is unsubstituted or substituted $C_1$-$C_{10}$ alkyl;

reacting the compound of formula VII with a compound of formula VIII: $R^4$—X (VIII) in the presence of a metal to produce a reaction mixture, wherein X is halo and $R_4$ is unsubstituted or substituted $C_1$-$C_{10}$ alkyl, unsubstituted or substituted $C_3$-$C_{20}$ cycloalkyl, unsubstituted or substituted $C_2$-$C_{10}$ alkenyl, or unsubstituted or substituted aryl; and optionally treating the reaction mixture with an acid and/or heat to obtain the compound of formula V.

In one embodiment, $R_4$ is substituted or unsubstituted alkyl having 1, 2, 3, 4, 5, 6, 7, 8, 9, or 10 carbon atoms, or $R_4$ is substituted or unsubstituted alkenyl having 2, 3, 4, 5, 6, 7, 8, 9, or 10 carbon atoms and one, two, or three carbon-carbon double bonds. For example, $R_4$ is unsubstituted $C_1$-$C_{10}$ alkyl or unsubstituted $C_2$-$C_{10}$ alkenyl.

In one embodiment, $R_6$ is substituted or unsubstituted alkyl having 1, 2, 3, 4, 5, 6, 7, 8, 9, or 10 carbon atoms, or $R_6$ is substituted or unsubstituted alkenyl having 2, 3, 4, 5, 6, 7, 8, 9, or 10 carbon atoms and one, two, or three carbon-carbon double bonds. For example, $R_6$ is unsubstituted $C_1$-$C_{10}$ alkyl or unsubstituted $C_2$-$C_{10}$ alkenyl.

In one embodiment, $R_5$ is substituted or unsubstituted alkyl having 10, 11, 12, 13, 14, 15, 16, 17, 18, 19, or 20 carbon atoms, or $R_5$ is substituted or unsubstituted alkenyl having 10, 11, 12, 13, 14, 15, 16, 17, 18, 19, or 20 carbon atoms and one, two, three, or more carbon-carbon double bonds. For example, $R_5$ is unsubstituted $C_{10}$-$C_{20}$ alkyl or unsubstituted $C_{10}$-$C_{20}$ alkenyl.

In one embodiment, X is Cl or Br.

In one embodiment, the compound of formula VI is fatty acid or an ester thereof, e.g., a component of meadowfoam seed oil.

In one embodiment, the compound of formula VII is methyl 5-oxopentanoate.

In one embodiment, the compound of formula V is 6-allyltetrahydro-2H-pyran-2-one.

In one embodiment, the compound of formula VIII is 3-bromoprop-1-ene or 3-chloroprop-1-ene.

In one embodiment, the reaction of the compound of formula VI with ozone is carried out in the presence of a solvent. For example, the solvent comprises water, an organic solvent or a mixture there of. For example, the organic solvent comprises an organic acid, e.g., an acid acetic acid, propionic acid, butyric acid, nonanoic acid, a fatty acid, or a mixture thereof.

In one embodiment, the reaction of the compound having the formula VI with ozone is carried out in the absence of a solvent.

In one embodiment, the reaction of the compound of formula VI with ozone is reductive ozonolysis, namely, the compound of formula VI reacting with ozone and subsequently reacting with a reductant (i.e., a reducing agent). For example, the reductant used in the method is a reducing agent suitable for producing an aldehyde in a reductive ozonolysis process. For example, the reductant is $H_2$ in the presence or absence of a suitable catalyst, such as Pd, Ni, Rh, Pt, or Ru. For example, the reductant is sodium bisulfite ($NaHSO_3$). For example, the reductant is triphenylphosphine, thiourea, zinc dust, or dimethyl sulfide.

In one embodiment, the metal is zinc, lithium, magnesium, or copper.

In one embodiment, the reaction mixture from reacting the compound of formula VII and the compound of formula VIII is treated with an acid (e.g., hydrochloric acid), heat, or both, to obtain the compound of formula V.

In one embodiment, the reaction mixture from reacting the compound of formula VII and the compound of formula VIII is not treated with an acid or heat to obtain the compound of formula V.

Examples of the methods of the invention are illustrated as in Schemes 1 and 2 below. Variables such as $R_1$ through $R_6$, X, and Y in Schemes 1 and 2 are as defined herein for formulae I-VIII unless otherwise specified. Scheme 1 below illustrates a synthetic route of producing an unsaturated delta-lactone from ricinoleic acid and/or an ester thereof Scheme 1

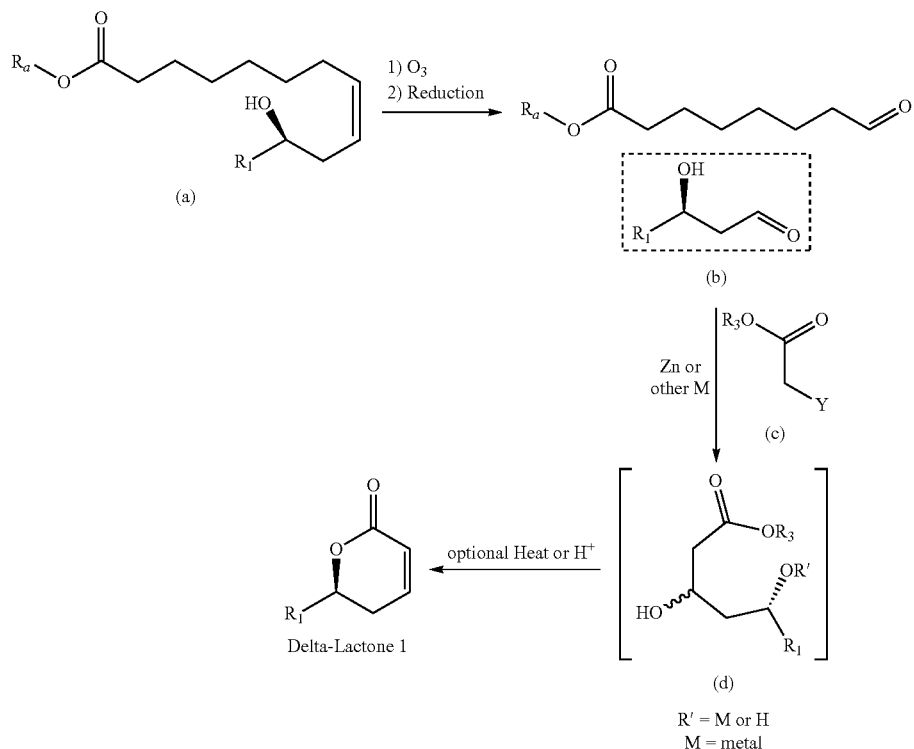

In Scheme 1 above, compound (b) (e.g., 3-(R)-hydroxynonanal when $R_1$ is hexyl) is generated by reductive ozonolysis of a fatty acid (a) or an ester thereof (e.g., ricinoleic acid when $R_1$ is hexyl); next, an alkylmetal halide (c) generated in situ from a metal and 2-haloacetate, such as 2-ethoxy-(2-oxoethyl)zinc(II) bromide, can then insert into the aldehyde functionality to from a hydroxyl anion intermediate (d), which can undergo intramolecular cyclization with the corresponding ester or acid, either directly or after addition of heat and/or acid catalyst to generate the desired 5-substituted delta-lactone 1 (e.g., (R)-6-hexyl-5,6-dihydro-2H-pyran-2-one when $R_1$ is hexyl).

In one embodiment, a mixture of castor oil, water, and an organic acid (e.g., acetic acid) reacts with ozone, followed by reacting with hydrogen, optionally with the presence of a catalyst (e.g., Pd), until all peroxide has been consumed (e.g., according to a titrated starch-iodine test); the organic phase of the resulting mixture is then separated and distilled to afford 3-(R)-hydroxynonanal; then, a suspension of zinc in tetrahydrofuran is stirred at reflux, while adding dropwise a mixture of 3-(R)-hydroxynonanal and ethyl bromoacetate dissolved in tetrahydrofuran to the stirring reaction mixture; next, the reaction mixture is acidified and then refluxed to remove the organic solvent; next, the remaining aqueous solution is extracted with an organic solve such as ethyl acetate, and the resulting organic phase is concentrated and then purified to afford (R)-6-hexyl-5,6-dihydro-2H-pyran-2-one.

More specifically, a mixture of castor oil, water, and acetic acid is cooled to, e.g., 20° C. in a jacketed reactor while stirring. Ozone (e.g., about 6-7% by weight in oxygen) is then diffused into the mixture, at e.g., 10 L/min for 100 minutes, and the reaction temperature is maintained at, e.g., 32° C. or lower. The reaction vessel is then purged with $N_2$ and the reaction mixture is transferred into a high-pressure reactor and charged with palladium black (e.g., 0.15% by weight). The reaction mixture is then stirred under hydrogen atmosphere (e.g., 350 psi) at e.g., 75° C. for e.g., 150 minutes until all peroxide is consumed according to a titrated starch-iodine test. The reaction mixture is then cooled down and filtered to remove the catalyst and the filtrate is placed in a separatory funnel. The organic phase is separated and distilled using, e.g., a 2" wiped film, short-path distillation unit at e.g., 5 mbar pressure, e.g., 60° C. jacket temperature, and e.g., 0° C. condenser temperature. A second distillation of the crude residue at e.g., 5 mbar pressure, e.g., 90° C. jacket temperature, and e.g., 0° C. condenser temperature affords 3-(R)-hydroxynonanal as a mixture of monomer and diastereomeric dimers. Next, a suspension of zinc in tetrahydrofuran is stirred at reflux, while adding dropwise a mixture of 3-(R)-hydroxynonanal and ethyl bromoacetate dissolved in tetrahydrofuran to the stirring reaction mixture over e.g., 5 hours. The reaction mixture is then cooled down in an ice bath and 1N(aq.) HCl is slowly added to acidify the reaction mixture to a pH of e.g., 2. The resulting reaction mixture is then refluxed overnight. The next day the organic solvent is evaporated and the remaining aqueous solution is extracted with ethyl acetate. The organic phase is concentrated to yield a crude material, which is dissolved in toluene and refluxed for an additional e.g., 3 hours. Removal of the solvent affords a crude material, which is purified using silica gel chromatography (e.g., with 0 to 20% gradient of ethyl acetate in heptane) to afford (R)-6-hexyl-5,6-dihydro-2H-pyran-2-one. Unexpectedly, using Zn as the metal is particularly useful in preventing side reactions, such as elimination and addition to the ester, from taking place. This has the added benefit of allowing the stereochemistry imbued in the ricinoleic acid-derived aldehyde to be retained so that enantio-enriched product can be obtained.

Scheme 2 below illustrates a synthetic route of producing a saturated delta-lactone from a fatty acid or an ester thereof having a C—C double bond at the 5-position.

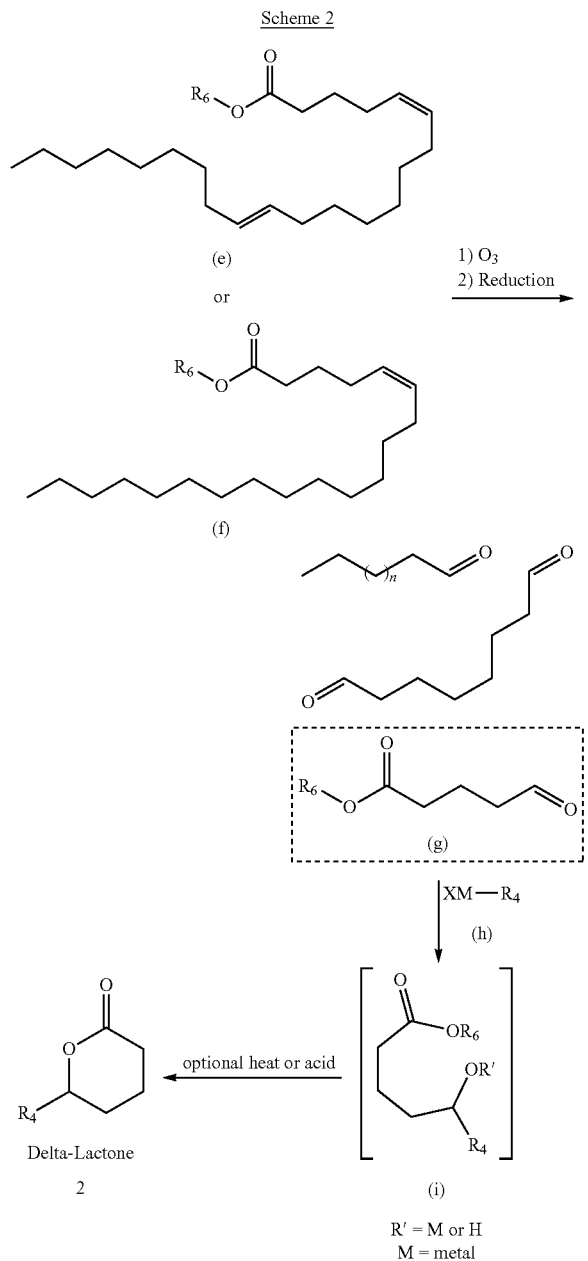

In Scheme 2 above, 5-oxopentanoate (g) (e.g., methyl 5-oxopentanoate when $R_6$ is methyl) is first generated via reductive ozonolysis of esters of components (e) and (f) found in meadowfoam seed oil; next, an alkylmetal halide (h) generated in situ from a metal M and $R_4$—X in which X is halo and $R_4$ is alkyl, alkenyl, cycloalkyl, aryl, or the like, such as allylzinc (II) bromide, can insert into the aldehyde to form a hydroxyl anion intermediate (i), which can undergo intramolecular cyclization with the corresponding ester or acid, either directly or after addition of heat and/or acid catalyst to afford desired 5-substituted delta-lactone 2 (e.g., 6-allyltetrahydro-2H-pyran-2-one when $R_4$ is allyl).

In one embodiment, a mixture of methyl ester of meadowfoam seed oil, water and acetic acid reacts with ozone, followed by reacting with hydrogen, optionally with the presence of a catalyst (e.g., Pd), until all peroxide has been consumed (e.g., according to a titrated starch-iodine test); the organic layer of reaction mixture is then removed and the remaining aqueous layer, which contains acetic acid, is treated with brine to form a new, clear organic layer, which is separated, washed (e.g., with brine and/or 10% aqueous $Na_2CO_3$ to afford a crude material, which includes methyl 5-oxopentanoate as a major product.

More specifically, a mixture of methyl ester of meadowfoam seed oil, water and acetic acid is stirred at e.g., 20° C. in a jacketed reactor. Ozone (e.g., about 6-7% by weight in oxygen) is then diffused into the mixture at, e.g., 10 L/min for about 90 minutes, and the reaction temperature is maintained at e.g., 32° C. or lower. The reaction vessel is then purged with $N_2$ and the reaction mixture is transferred into a high-pressure reactor and charged with palladium black (e.g., 0.15% by weight). The reaction mixture is stirred under hydrogen atmosphere (e.g., 350 psi) at e.g., 75° C. for e.g., 150 minutes until all peroxide has been consumed according to a titrated starch-iodine test. The reaction mixture is then cooled down and filtered to remove the catalyst and the filtrate is placed in a separatory funnel. The layers separate and the organic layer is removed. The remaining aqueous layer, which contains acetic acid, is treated with brine. A new, clear organic layer forms which is separated, washed with brine, and washed with e.g., 10% aqueous $Na_2CO_3$. A crude material is obtained, which includes methyl 5-oxopentanoate as a major product, in addition to minor amounts of alkyl aldehyde.

In one embodiment, the 5-substituted delta-lactone product from the method of the invention can be >80% pure (e.g., >85%, >90%, >92%, >95%, >97%, >98%, >98.5%, or >99% pure). $^1$H NMR and gas chromatography can be used to characterize the desired 5-substituted delta-lactone product. For example, the 5-substituted delta-lactone product is free of undesired byproduct or starting material. For example, the impurities (e.g., the starting material fatty acids such as ricinoleic acid and methyl ester of meadowfoam seed oil, or aldehydic product such as 3-(R)-hydroxynonanal and 5-oxopentanoate) in the 5-substituted delta-lactone product is less than 20% (e.g., <15%, <10%, <8%, <5%, <3%, <2%, <1.5%, or <1%).

In one embodiment, the ozone used in the ozonolysis is generated by electrolyzing water.

In some embodiments, the product of the method of the invention has an overall yield of no less than 60%, e.g., no less than 70%, no less than 80%, no less than 90%, or no less than 95%.

In some embodiments, the product of the method of the invention contains more than 80% of a compound of formula I. In some embodiments, the product of the method of the invention contains more than 85%, 90%, 92%, 95%, 97%, 98%, 98.5%, or 99% of a compound of formula I. For example, the product is free of undesired byproduct or starting material. For example, the impurities (e.g., undesired byproduct or starting material such as ricinoleic acid, or 3-(R)-hydroxynonanal) in the 5-substituted delta-lactone product is less than 20% (e.g., <15%, <10%, <8%, <5%, <3%, <2%, <1.5%, or <1%).

In some embodiments, the product of the method of the invention contains more than 80% of a compound of formula V. In some embodiments, the product of the method of the invention contains more than 85%, 90%, 92%, 95%, 97%, 98%, 98.5%, or 99% of a compound of formula V. For example, the product is free of undesired byproduct or starting material. For example, the impurities (e.g., undesired byproduct or starting material such as fatty acid components of meadowfoam seed oil and esters thereof, or 5-oxopentanoate) in the 5-substituted delta-lactone product is less than 20% (e.g., <15%, <10%, <8%, <5%, <3%, <2%, <1.5%, or <1%).

It will be appreciated that the methods disclosed herein are suitable for both large-scale and small-scale preparations of the desired compounds. In preferred embodiments of the methods described herein, the compounds of formula I or compounds of formula V may be prepared on a large scale, for example on an industrial production scale rather than on an experimental/laboratory scale. For example, the methods described herein allow for the preparation of batches of at least 1 g, or at least 5 g, or at least 10 g, or at least 100 g, or at least 1 kg, or at least 10 kg, or at least 100 kg of product.

The details of one or more embodiments of the invention are set forth in the accompanying description below. Unless defined otherwise, all technical and scientific terms used herein have the same meaning as commonly understood by one of ordinary skill in the art to which this invention belongs. In the case of conflict, the present specification will control.

Unless otherwise indicated, it is to be understood that the terminology used herein is for the purpose of describing particular embodiments only and is not intended to be limiting. In this specification and in the claims that follow, reference will be made to a number of terms, which shall be defined to have the definitions set forth below.

As used herein, the singular forms "a," "an," and "the" include plural referents unless the context clearly dictates otherwise. Thus, for example, reference to "a reactant" includes not only a single reactant but also a combination or mixture of two or more different reactant, reference to "a substituent" includes a single substituent as well as two or more substituents, and the like.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

As used herein, the phrase "of the formula", "having the formula" or "having the structure" is not intended to be limiting and is used in the same way that the term "comprising" is commonly used.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule* of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116). In some formulae of the present application, one or more chiral centers are identified by an asterisk placed next to the chiral carbon. In other formulae, no chiral center is identified, but the chiral isomers are nonetheless covered by these formulae.

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Some compounds of the present invention can exist in a tautomeric form which is also intended to be encompassed within the scope of the present invention. "Tautomers" refers to compounds whose structures differ markedly in arrangement of atoms, but which exist in easy and rapid equilibrium. It is to be understood that the compounds of the invention may be depicted as different tautomers. It should also be understood that when compounds have tautomeric forms, all tautomeric forms are intended to be within the scope of the invention, and the naming of the compounds does not exclude any tautomeric form. Further, even though one tautomer may be described, the present invention includes all tautomers of the present compounds.

As used herein, the term "salt" can include acid addition salts including hydrochlorides, hydrobromides, phosphates, sulfates, hydrogen sulfates, alkylsulfonates, arylsulfonates, acetates, benzoates, citrates, maleates, fumarates, succinates, lactates, and tartrates; alkali metal cations such as $Na^+$, $K^+$, $Li^+$, alkali earth metal salts such as $Mg^{2+}$ or $Ca^{2+}$, or organic amine salts, or organic phosphonium salts.

The term "alkyl" as used herein refers to a branched or unbranched saturated hydrocarbon group typically although not necessarily containing 1 to about 20 carbon atoms, such as methyl, ethyl, n-propyl, isopropyl, n-butyl, isobutyl, t-butyl, octyl, and the like.

The term "alkenyl" as used herein refers to a branched or unbranched unsaturated hydrocarbon group typically although not necessarily containing 2 to about 20 carbon atoms and 1-8 carbon-carbon double bonds, such as ethylene, n-propylene, isopropylene, n-butylene, isobutylene, t-butylene, octylene, and the like.

The term "aryl" refers to a $C_6$-$C_{14}$ aromatic carbocyclic ring structure having a single ring or a multiple fused ring. In some embodiments, the aryl ring may be fused to a non-aromatic ring, as long as the point of attachment to the core structure is through the aromatic ring. Aryl groups include, but are not limited to, phenyl, biphenyl, and naphthyl.

The term "alkylmetal halide" as used herein refers to a compound having the formula of XM-R in which X is halo such as F, Cl, Br, or I, M is a metal such as a transition metal, an alkali metal or an alkali earth metal, and R is unsubstituted or substituted alkyl, unsubstituted or substituted alkenyl, unsubstituted or substituted cycloalkyl, unsubstituted or substituted aryl, or the like.

By "substituted" as in "substituted alkyl," "substituted alkenyl," "substituted aryl," and the like, it is meant that in the alkyl, alkenyl, aryl, or other moiety, at least one hydrogen atom bound to a carbon atom is replaced with one or more non-hydrogen substituents, e.g., by a functional group.

Examples of functional groups include, without limitation: halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—N$^+$≡C$^-$), cyanato (—O—C≡N), isocyanato (—O—N$^+$≡C$^-$), isothiocyanato (—S—C≡N), azido (—N$^+$=N$^+$=N$^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O$^-$) 2), phosphinato (—P(O)(O$^-$)), phospho (—$PO_2$), phosphino (—$PH_2$), mono- and di-($C_1$-$C_{24}$ alkyl)-substituted phosphino, mono- and di-($C_5$-$C_{20}$ aryl)-substituted phosphino; and the hydrocarbyl moieties such as $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above.

In the present specification, the structural formula of the compound represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula. It is noted that any crystal form, crystal form mixture, or anhydride or hydrate thereof is included in the scope of the present invention.

All percentages and ratios used herein, unless otherwise indicated, are by weight.

EXAMPLES

Example 1: Synthesis of 3-(R)-Hydroxynonanal

A mixture of castor oil (400 g), water (400 g), and acetic acid (400 g) were cooled to 20° C. in a jacketed reactor while stirring. A ~6-7% by weight stream of $O_3$ in $O_2$ was diffused into the mixture at a flow rate of 10 L/min for 100 minutes, while maintaining a reaction temperature not exceeding 32° C. The reaction vessel was then purged with $N_2$ and the reaction mixture was transferred into a high-pressure reactor and charged with Palladium black (0.15% by weight). The reaction mixture was stirred under hydrogen atmosphere (350 psi) at 75° C. for 150 minutes until all peroxide had been consumed according to a titrated starch-iodine test. The reaction mixture was then cooled down and filtered to remove the catalyst and the filtrate was placed in a separatory funnel. The organic phase was separated and distilled using a 2" wiped film, short-path distillation unit at 5 mbar pressure, 60° C. jacket temperature, and 0° C. condenser temperature. A second distillation of the crude residue at 5 mbar pressure, 90° C. jacket temperature, and 0° C. condenser temperature afforded 3-(R)-hydroxynonanal as a mixture of monomer and diastereomeric dimers (56.4 g), see, e.g., Kula, J. et al. *Tetrahedron: Asymmetry* 11 (2000) 943-950. This material was carried on to the next step without further purification.

Example 2: Synthesis of (R)-6-hexyl-5,6-dihydro-2H-pyran-2-one

A suspension of zinc (4.58 g, 70 mmol) in THF (300 ml) was stirred at reflux, while adding dropwise a mixture of 3-(R)-hydroxynonanal (5.54 g, 35 mmol) and ethyl bromoacetate (11.7 g, 70 mmol) dissolved in THF (200 ml) to the stirring reaction mixture over 5 hours. The reaction mixture was then cooled down in an ice bath and ~100 ml $1N_{(aq.)}$ HCl was added to acidify the reaction mixture to a pH of 2 (gas formed initially during the slow addition). The resulting reaction mixture was refluxed overnight. The next day the organic solvent was evaporated and the remaining aqueous solution was extracted with ethyl acetate. The organic phase was concentrated to yield a crude material, which was dissolved in toluene (100 ml) and refluxed for an additional 3 hours. Removal of the solvent afforded a crude material (6.5 g), which was purified using silica gel chromatography (0 to 20% gradient of ethyl acetate in heptane) to afford (R)-6-hexyl-5,6-dihydro-2H-pyran-2-one. $^1$H NMR (CDCl$_3$, 400 MHz) δ 0.88 (m, J=6.8 Hz, 3H, —$CH_3$), 1.21-1.44 (m, 7H, —$CH_2$—), 1.45-1.57 (m, 1H, —$CH_2$—), 1.59-1.68 (m, 1H, —$CH_2$—), 1.75-1.84 (m, 1H, —$CH_2$—), 2.31-2.34 (m, 2H, —$CH_2$—), 4.38-4.45 (m, 1H, —CHO—), 5.99-6.03 (m, 1H, =CH—), 6.85-6.89 (m, 1H, =CH—). See, e.g., Dupe et al., *ChemSusChem.* 2012, 5, 2249-2254.

Example 3: Synthesis of Methyl 5-Oxopentanoate

A mixture of methyl ester of meadowfoam seed oil (300 g), water (300 g) and acetic acid (300 g) was stirred at 20°

C. in a jacketed reactor. A ~6-7% by weight stream of $O_3$ in $O_2$ was passed through the solution at 10 L/min for ~90 minutes, while maintaining a reaction temperature not exceeding 32° C. The reaction vessel was then purged with $N_2$ and the reaction mixture was transferred into a high-pressure reactor and charged with Palladium black (0.15% by weight). The reaction mixture was stirred under hydrogen atmosphere (350 psi) at 75° C. for 150 minutes until all peroxide had been consumed according to a titrated starch-iodine test. The reaction mixture was then cooled down and filtered to remove the catalyst and the filtrate was placed in a separatory funnel. The layers separated and the organic layer was removed. The remaining aqueous layer, which contained acetic acid, was then treated with brine. A new, clear organic layer formed which was separated, washed with brine, and washed with 10% aqueous $Na_2CO_3$. A crude material was obtained, which included methyl 5-oxopentanoate as major product, along with minor amounts of alkyl aldehyde (12 g). $^1$H NMR (CDCl$_3$, 400 MHz) δ 1.95 (tt, J=7.2 Hz, J=7.6 Hz, 2H, —CH$_2$—), 2.37 (t, J=7.2 Hz, 2H, —CH$_2$—), 2.53 (dt, J=1.2 Hz, J=7.6 Hz, 2H, —CH$_2$—), 9.76 (t, J=1.2 Hz 1H, —CHO). See, e.g., Cook et al., *J. Org. Chem.* 2012, 77, 6728-6742.

Example 4: Synthesis of 6-Allyltetrahydro-2H-pyran-2-one

6-Allyltetrahydro-2H-pyran-2-one was prepared according to a procedure similar to that described in Example 2 using 5-oxopentanoate as the corresponding starting material. $^1$H NMR (CDCl$_3$, 500 MHz) δ 1.50-1.59 (m, 1H, —CH$_2$—), 1.79-1.87 (m, 1H, —CH$_2$—), 1.89-1.96 (m, 2H, —CH$_2$—), 2.35-2.51 (m, 3H, —CH$_2$—), 2.55-2.61 (m, 1H, —CH$_2$—), 4.31-4.36 (m, 1H, —CHO—), 5.11-5.17 (m, 2H, =CH$_2$), 5.77-5.86 (m, 1H, =CH—). See, e.g., Utaka et al., A. *J. Org. Chem.* 1986, 51, 935-938.

INCORPORATION BY REFERENCE

The entire disclosure of each of the patent documents and scientific articles referred to herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of producing a compound of formula A,

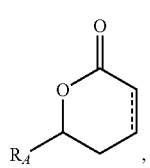
(A)

wherein the ===== is a single bond or a double bond and $R_4$ is unsubstituted or substituted $C_1$-$C_{10}$ alkyl, unsubstituted or substituted $C_3$-$C_{20}$ cycloalkyl, unsubstituted or substituted $C_2$-$C_{10}$ alkenyl, or unsubstituted or substituted aryl; the method comprising:

(i) when the compound of formula A is of formula I:

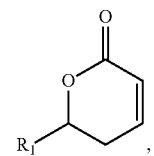
(I)

reacting a compound of formula II:

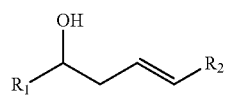
(II)

with ozone to obtain a compound of formula III;

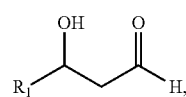
(III)

wherein $R_1$ is unsubstituted or substituted $C_1$-$C_{10}$ alkyl, unsubstituted or substituted $C_3$-$C_{20}$ cycloalkyl, unsubstituted or substituted $C_2$-$C_{10}$ alkenyl, or unsubstituted or substituted aryl and $R_2$ is H, unsubstituted or substituted $C_1$-$C_{20}$ alkyl, or unsubstituted or substituted $C_2$-$C_{20}$ alkenyl;

reacting the compound of formula III with a compound of formula IV:

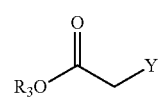
(IV)

in the presence of a metal to produce a reaction mixture, wherein Y is halo and $R_3$ is unsubstituted or substituted $C_1$-$C_{20}$ alkyl unsubstituted or substituted $C_2$-$C_{20}$ alkenyl, or unsubstituted or substituted aryl; and optionally treating the reaction mixture with an acid and/or heat to obtain the compound of formula I wherein $R_1$ is unsubstituted or substituted $C_1$-$C_{10}$ alkyl, unsubstituted or substituted $C_3$-$C_{20}$ cycloalkyl, unsubstituted or substituted $C_2$-$C_{10}$ alkenyl, or unsubstituted or substituted aryl; or alternatively, (ii) when the compound of formula A is of formula V:

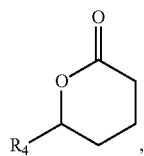
(V)

reacting a compound of formula VI

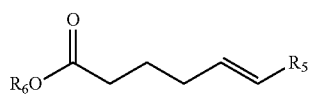
(VI)

with ozone to obtain a compound of formula VII;

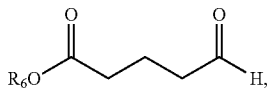
(VII)

wherein $R_5$ is unsubstituted or substituted $C_1$-$C_{20}$ alkyl or unsubstituted or substituted $C_2$-$C_{20}$ alkenyl and $R_6$ is unsubstituted or substituted $C_1$-$C_{10}$ alkyl;
reacting the compound of formula VII with a compound of formula VIII: $R_4$—X (VIII) in the presence of a metal to produce a reaction mixture, wherein X is halo and $R_4$ is unsubstituted or substituted $C_1$-$C_{10}$ alkyl, unsubstituted or substituted $C_3$-$C_{20}$ cycloalkyl, unsubstituted or substituted $C_2$-$C_{10}$ alkenyl, or unsubstituted or substituted aryl; and
optionally treating the reaction mixture with an acid and/or heat to obtain the compound of formula V wherein $R_4$ is unsubstituted or substituted $C_1$-$C_{10}$ alkyl, unsubstituted or substituted $C_3$-$C_{20}$ cycloalkyl, unsubstituted or substituted $C_2$-$C_{10}$ alkenyl, or unsubstituted or substituted aryl.

2. The method of claim 1, wherein the compound of formula A is of formula I wherein $R_1$ is unsubstituted or substituted $C_1$-$C_{10}$ alkyl, unsubstituted or substituted $C_3$-$C_{20}$ cycloalkyl, unsubstituted or substituted $C_2$-$C_{10}$ alkenyl, or unsubstituted or substituted aryl, and the method comprises:
reacting a compound of formula II:

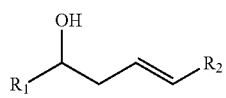
(II)

with ozone to obtain a compound of formula III;

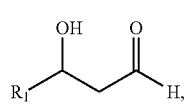
(III)

wherein $R_1$ is unsubstituted or substituted $C_1$-$C_{10}$ alkyl, unsubstituted or substituted $C_3$-$C_{20}$ cycloalkyl, unsubstituted or substituted $C_2$-$C_{10}$ alkenyl, or unsubstituted or substituted aryl and $R_2$ is H, unsubstituted or substituted $C_1$-$C_{20}$ alkyl, or unsubstituted or substituted $C_2$-$C_{20}$ alkenyl;
reacting the compound of formula III with a compound of formula IV:

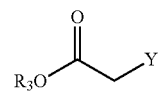
(IV)

in the presence of a metal to produce a reaction mixture, wherein Y is halo and $R_3$ is unsubstituted or substituted $C_1$-$C_{20}$ alkyl unsubstituted or substituted $C_2$-$C_{20}$ alkenyl, or unsubstituted or substituted aryl; and
optionally treating the reaction mixture with an acid and/or heat to obtain the compound of formula I.

3. The method of claim 2, $R_1$ is unsubstituted $C_1$-$C_{10}$ alkyl or unsubstituted $C_2$-$C_{10}$ alkenyl.

4. The method of claim 2, wherein $R_2$ is $C_1$-$C_{10}$ alkyl or $C_2$-$C_{10}$ alkenyl, each substituted with $COOR_a$, in which $R_a$ is H or unsubstituted or substituted $C_1$-$C_{10}$ alkyl.

5. The method of claim 2, wherein the compound of formula II is ricinoleic acid or an ester thereof.

6. The method of claim 2, wherein the compound of formula III is 3-hydroxynonanal or 3-(R)hydroxynonanal.

7. The method of claim 2, wherein the compound of formula I is 6-hexyl-5,6-dihydro-2H-pyran-2-one or (R)-6-hexyl-5,6-dihydro-2H-pyran-2-one.

8. The method of claim 2, wherein the compound of formula IV is ethyl bromoacetate or ethyl chloroacetate.

9. The method of claim 2, wherein the reaction of the compound of formula II with ozone is carried out in the presence of a solvent.

10. The method of claim 2, wherein the reaction of the compound having the formula II with ozone is carried out in the absence of a solvent.

11. The method of claim 1, wherein the compound of formula A is of formula V wherein $R_4$ is unsubstituted or substituted $C_1$-$C_{10}$ alkyl, unsubstituted or substituted $C_3$-$C_{20}$ cycloalkyl, unsubstituted or substituted $C_2$-$C_{10}$ alkenyl, or unsubstituted or substituted aryl, and the method comprises:
reacting a compound of formula VI

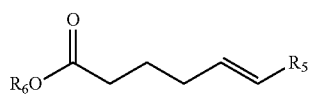
(VI)

with ozone to obtain a compound of formula VII;

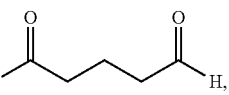
(VII)

wherein $R_5$ is unsubstituted or substituted $C_1$-$C_{20}$ alkyl or unsubstituted or substituted $C_2$-$C_{20}$ alkenyl and $R_6$ is unsubstituted or substituted $C_1$-$C_{10}$ alkyl;

reacting the compound of formula VII with a compound of formula VIII: $R_4$—X (VIII) in the presence of a metal to produce a reaction mixture, wherein X is halo and $R_4$ is unsubstituted or substituted $C_1$-$C_{10}$ alkyl, unsubstituted or substituted $C_3$-$C_{20}$ cycloalkyl, unsubstituted or substituted $C_2$-$C_{10}$ alkenyl, or unsubstituted or substituted aryl; and optionally treating the reaction mixture with an acid and/or heat to obtain the compound of formula V.

12. The method of claim 11, wherein $R_4$ is unsubstituted $C_1$-$C_{10}$ alkyl or unsubstituted $C_2$-$C_{10}$ alkenyl.

13. The method of claim 11, wherein the compound of formula VI is a fatty acid ester.

14. The method of claim 13, wherein the compound of formula VI is a component of meadowfoam seed oil.

15. The method of claim 11, wherein the compound of formula VII is methyl 5-oxopentanoate.

16. The method of claim 11, wherein the compound of formula V is 6-allyltetrahydro-2H-pyran-2-one.

17. The method of claim 11, wherein the compound of formula VIII is 3-bromoprop-1-ene or 3-chloroprop-1-ene.

18. The method of claim 11, wherein the reaction of the compound of formula VI with ozone is carried out in the presence of a solvent.

19. The method of claim 11, wherein the reaction of the compound having the formula VI with ozone is carried out in the absence of a solvent.

20. A compound of formula I produced by the method of claim 1.

21. A compound of formula V produced by the method of claim 11.

22. The method 13, wherein the compound of Formula VI is a fatty acid ester wherein $R_5$ is unsubstituted $C_{14}$ alkyl.

* * * * *